US007820836B2

(12) United States Patent
Rüttimann et al.

(10) Patent No.: US 7,820,836 B2
(45) Date of Patent: Oct. 26, 2010

(54) PROCESS FOR THE MANUFACTURE OF HYDROXYLATED ISOFLAVONES

(75) Inventors: August Rüttimann, Arlesheim (CH); Edith Maria Rüittmann-Wechsler, legal representative, Arlesheim (CH); Natalie Christina Rüittmann, legal representative, Arlesheim (CH); Pascal Michael Rüittmann, legal representative, Arlesheim (CH); Jochen Stangl, Wehr (DE)

(73) Assignee: DSM IP Assets B.V., Heerlen (NL)

( * ) Notice: Subject to any disclaimer, the term of this patent is extended or adjusted under 35 U.S.C. 154(b) by 121 days.

(21) Appl. No.: 11/918,220

(22) PCT Filed: Apr. 10, 2006

(86) PCT No.: PCT/EP2006/003252

§ 371 (c)(1),
(2), (4) Date: Dec. 30, 2008

(87) PCT Pub. No.: WO2006/111289

PCT Pub. Date: Oct. 26, 2006

(65) Prior Publication Data

US 2009/0287001 A1 Nov. 19, 2009

(30) Foreign Application Priority Data

Apr. 18, 2005 (EP) .................................. 05008389

(51) Int. Cl.
*C07D 311/36* (2006.01)
*C07C 45/45* (2006.01)
*C07C 49/11* (2006.01)

(52) U.S. Cl. ........................ 549/403; 568/322; 568/331

(58) Field of Classification Search ................. 549/403; 568/322, 331
See application file for complete search history.

(56) References Cited

FOREIGN PATENT DOCUMENTS

WO WO 2004/009576 A2 1/2004

OTHER PUBLICATIONS

Chang et al, "Microwave-Mediated synthesis of Anticarcinogenic Isoflavones from Soybeans", Journal of Agricultural and Food Chemistry, vol. 42, No. 9, 1994, pp. 1869-1871.
Ferro et al, "Synthesis of New Potential HIV-1 Integrase Inhibitors", Heterocycles, vol. 63, No. 12, Dec. 1, 2004, pp. 2727-2734.
Houben et al, "Uber die Kernkondensation von Phenolen und Phenolathern mit Nitrilen zu Phenol—Ketonen. II.: Synthese mit anisol, o-Brom-anisol, Phenotol, o-, m- und p-Kresylathern, Veratrol und Resorcin-ather" Chemische Berichte, vol. 60, No. 8, Sep. 21, 1927, pp. 1759-1778.
International Search Report mailed Jul. 24, 2006 in PCT/EP2006/003252.
Written Opinion mailed Jul. 24, 2006 in PCT/EP2006/003252.

*Primary Examiner*—Bernard Dentz
(74) *Attorney, Agent, or Firm*—Nixon & Vanderhye P.C.

(57) ABSTRACT

A process for the preparation of hydroxylated isoflavones by reacting in a Hoesch reaction using an alkanoic acid alkyl ester as solvent a phenol with a phenylacetonitrile to yield a 1,2-diphenyl-ethanone and transforming the ethanone into an isoflavone by well-known methods.

11 Claims, No Drawings

PROCESS FOR THE MANUFACTURE OF HYDROXYLATED ISOFLAVONES

This application is the US national phase of international application PCT/EP2006/003252 filed 10 Apr. 2006 which designated the U.S. and claims benefit of EP 05 008 389.8, dated 18 Apr. 2005, the entire content of which is hereby incorporated by reference.

The present invention relates to processes for the manufacture of hydroxylated isoflavones via 1,2-diphenylethanones which are obtained by a Hoesch reaction from phenols and hydroxylated phenylacetonitriles in which reaction a lower alkanoic acid lower alkyl ester is used as a solvent.

The hydroxylated isoflavones obtainable by the processes of the present invention are naturally occurring compounds exhibiting pharmacologically valuable activities and also known as phytoestrogens, such as daidzein (4',7-dihydroxy-isoflavone), prunetin (4',5-dihydroxy-7-methoxy-isoflavone), biochanin A (5,7-dihydroxy-4'-methoxy-isoflavone or genistein (4',5,7-trihydroxy-isoflavone), the latter being of specific interest in view of its valuable pharmacological activities, e.g. in the field of bone health and, more specifically, its use in the treatment of osteoporosis and related conditions.

Methods for the preparation of the hydroxylated isoflavones of the present invention are well-known and described in the prior art, e.g., in WO 02/085881 and WO 2004/009576. In these patent applications methods for the manufacture of hydroxylated isoflavones from 1,2-diphenyl-ethanones by reaction with mixed formic acid anhydrides are described.

On the other hand the preparation of 1,2-diarylethanones by acylation of aryl compounds with aryl-acetonitriles is well-known since long under the name Hoesch reaction (Chem. Ber. 48, 1122 [1915]). This reaction is generally conducted in ethyl ether in the presence of an acid catalyst, especially hydrochloric acid and/or a Lewis acid such as $ZnCl_2$, $FeCl_3$ or $AlCl_3$, with only moderate yields (about 50-60%), however. In 1927 J. Houben and W. Fischer in Ber. 60, p. 1763 state that only diethyl ether is a good solvent to be used in this reaction. They mention that except ether at the most acetic acid methyl ester (methyl acetate) is useful to some extent as solvent in that reaction with only very impure products obtainable, however. This, as has turned out now and as applicants have found was a prejudice which obviously has prevailed for nearly eighty years.

Chinese patent No. CN 1048716 C describes the preparation of 2,4-dihydroxyphenyl-benzyl-ketone from resorcin and phenylacetonitrile in 1,2-dichloroethane and glycol dimethylether in the presence of anhydrous zinc chloride, avoiding ethyl ether as solvent.

WO 03/053900 describes a method for producing 1,2-diaryl-ethanones by reacting an arylacetonitrile with an aromatic compound and by hydrolysing the isolated ketimine intermediate using as solvent a dialkyl ether of a mono- or polyalkylene glycol or a cyclic ether with at least two oxygen atoms. Yields of up to 84% are obtained.

It was an objective of the present inventors to find and develop a method for the manufacture of 1,2-diphenylethanones and of corresponding hydroxylated isoflavones useful for the commercial production of these compounds in an economically and ecologically advantageous way avoiding disadvantages of prior art processes, e.g. the use of ethers or glycols.

This objective has been achieved by using lower alkanoic acid lower alkyl esters, i.e. $C_{1-5}$-alkanoic acid $C_{1-5}$-alkyl esters, preferably methyl acetate and ethyl acetate, as solvents in the Hoesch reaction. In view of the existing prejudice mentioned above this achievement was surprising and unobvious.

The present invention in one embodiment relates to a process for manufacturing a hydroxylated isoflavone of the general formula

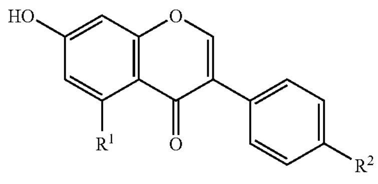

I wherein $R^1$ is hydrogen or hydroxy and $R^2$ is hydroxy or $C_{1-6}$-alkoxy, by reacting in a Hoesch reaction using a $C_{1-5}$-alkanoic acid $C_{1-5}$-alkyl ester as solvent a phenol of the formula

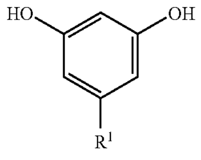

II with a phenylacetonitrile of the formula

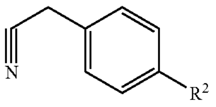

III to yield a 1,2-diphenyl-ethanone of formula

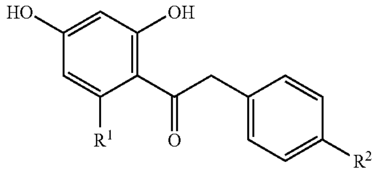

IV and further transforming the 1,2-diphenyl-ethanone into a compound of formula I.

In another embodiment the present invention relates to a process for the preparation of the 1,2-diphenyl-ethanones of formula IV by reacting in a Hoesch reaction using a $C_{1-5}$-alkanoic acid $C_{1-5}$-alkyl ester as solvent a phenol of the formula II with a phenylacetonitrile of formula III as defined above.

Examples of $C_{1-5}$-alkanoic acids are formic, acetic, propionic and isopropionic acids. Examples of $C_{1-5}$-alkyl esters are methyl, ethyl, propyl, isopropyl, butyl, isobutyl and tert.-butyl esters. The preferred solvents of the present invention are methylacetate and ethylacetate.

Examples of $C_{1-6}$-alkoxy groups present in phenylacetonitriles of formula III are methoxy, ethoxy, propoxy, isopropoxy, butoxy, isobutoxy, tert.-butoxy, pentyloxy and hexyloxy.

The term "hydroxylated isoflavones" used in connection with the present invention comprises compounds which occur naturally as components of plants, possibly in the form of glycosides, or compounds synthetically prepared. The preferred hydroxylated isoflavones of the present invention are those which exhibit valuable pharmacological activities, are part of food or animal feed, and are or can be used as medicaments or additives for food and animal feed.

The starting compounds used in the Hoesch reaction, i.e. the phenols of formula II and the phenylacetonitriles of formula III, are well-known and/or easily available by methods well-known in the art.

The first reaction step of the Hoesch reaction of the present invention is sensitive to water. The yield decreases with increasing concentration of water in the reaction mixture. Therefore, the water content of the raw materials for this step should be as low as possible. However, there is no absolute figure for the limit of the water content of the raw materials. Advantageously the materials, e.g. phloroglucinol, are used in anhydrous form. The water content of the alkanoic acid ester solvents, e.g. of ethyl and methyl acetate, is preferably below 0.1%.

The reaction of the phenol with the phenylacetonitrile can be conducted with equimolar amounts. However, it is advantageous to use the nitrile in excess. In case of p-hydroxyphenylacetonitrile and phloroglucinol an excess of 10% has proven to be optimal.

To the mixture of the reactants in the solvent the acid catalyst which is conventionally gaseous hydrogen chloride or a Lewis acid is added. In case of gaseous hydrogen chloride the reaction mixture is cooled advantageously to a temperature of 0-10° C., preferably to 5° C. or below, and the hydrogen chloride is introduced.

Although the amount of solvent used in the reaction is not critical it is advantageous to use as little as possible. Best results are obtained with an amount of solvent which keeps the reaction mixture just stirable. In case of phloroglucinol this is about 1 l for about 2.2 moles of phloroglucinol. The result of working with a minimum of the solvent—apart from lower costs for the solvent—is: quicker reaction, higher yield of the ketimine, lower amount of gaseous hydrochloric acid and, consequently, of neutralization agent needed.

While the prior art teaches the use of a high excess of gaseous hydrochloric acid and isolation of the intermediate ketimine it turned out that use of only 2 to 4 equivalents are sufficient and not isolating the intermediate ("through process") before hydrolysis yields best results.

The hydrolysis of the ketiminium salt, i.e. of the hydrochloride, is effected by addition of water and a base to neutralize the hydrochloric acid to a pH of 4. At higher pH the formation of side reactions increases with an increase of impurities in the reaction product obtained. The concentration of the aqueous alkali solution is not critical. Preferably 20-35%, w/w, sodium or potassium hydroxide or ammonia is used. It is furthermore advantageous to distill off the solvent, then to add ethanol as solution aid and to heat the reaction mixture to reflux. Under these conditions the ketiminium salt which is little soluble in the alkanoic acid ester is gradually dissolved and hydrolysed to yield the 1,2-diphenyl-ethanone. The ethanol is distilled of thus reducing the solubility of the ethanone which is allowed to crystallize from the cooled solution in high purity and, if desired, further purified to more than 98% by conventional methods such as recrystallization.

In accordance with an embodiment of the present invention the 1,2-diphyenyl-ethanones of formula IV are transformed into hydroxylated isoflavones of formula I. This can be done by methods well known in the art, e.g. by reaction with a formic acid/sulfuric acid anhydride salt of formula

V

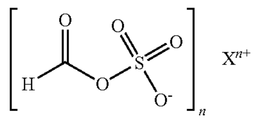

wherein n is an integer of 1 to 4 and

X is a metallic or ammonium cation,
 an amine salt, a salt of a heterocyclic base,
 a quaternary ammonium or phosphonium salt
 including polymeric or polymer bound forms thereof, as described in WO 02/085881, the contents of which reference are hereby incorporated into the present specification.

Alternatively, the 1,2-diphenyl-ethanones of formula IV can be transformed into hydroxylated isoflavones of formula I by reaction with a mixed formic acid anhydride of formula

VI

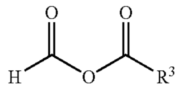

wherein $R^3$ is $C_{2-20}$-alkyl, $C_{1-6}$-haloalkyl, $C_{1-6}$-alkoxy)methyl, carboxy-$C_{2-6}$-alkyl, aryl-$C_{1-6}$-alkyl, a group $—CH_2—(OCH_2CH_2)_m—O—C_{1-6}$-alkyl, a group $—CH(R^4)═CR^5R^6$, —CH═CH—COOH, $C_{3-8}$-cycloalkyl, aryl, heteroaryl, di($C_{1-6}$-alkyl)aminomethyl, diarylaminomethyl, a group $—(CH_2)_n—COOR^7$, a group $—(CH_2)_m—COOCHO$, —CH═CH—COOCHO, $C_{1-6}$-alkoxy, aryloxy or formyloxy;

$R^4$-$R^7$, independently from each other, being hydrogen, $C_{1-6}$-alkyl or aryl;

m is an integer from 1 to 4 and n is an integer from 1 to 8, preferably with formic acid/propionic acid anhydride and formic acid/isobutyric acid anhydride as descried in WO 2004/009576, the contents of which are hereby incorporated into the present specification.

The present invention is described in still more detail by the following examples.

EXAMPLE 1

In a 500 ml double-walled reaction vessel equipped with a magnetic stirrer, a dip tube, a distillation column, argon gasification means, a thermometer and a thermostat, 39 g of phloroglucinol (99%, 0.3 mole) and 45 g of p-hydroxyphenyl-acetonitrile (99.4%, 0.33 mole) were solved in 130 g of ethylacetate at room temperature. The solution was cooled to 5° C. Within 60 minutes at 5-10° C. 42 g of gaseous hydrogen chloride (1.14 mole; 3.8 equiv.) were introduced. After 18 hours of stirring the mixture was poured onto 300 g of ice/water and brought to a pH of 4.0 by addition of 95 g of 28% aqueous sodium hydroxide solution.

The solution was heated to about 75° C. and about 130 g of ethyl acetate were distilled off within 120 minutes. Since the temperature had risen to 101° C. the mixture was cooled to 80° C. and to the resulting suspension were added 100 g of technical ethanol. The mixture was stirred for 5 hours under reflux. After 4 hours a dark yellow solution was obtained. The ethanol was distilled off within an hour. After cooling to 20° C. and standing over night the phloroacetophenone crystallized. Filtration, washing with 80 ml of water and drying at 80° C./1 mbar (0.1 kPa) for 4 hours yielded 51.7 g of a yellow product in a yield of 64% (97% purity by HPLC).

EXAMPLE 2

102 kg of methyl acetate, 32.6 kg of phloroglucinol (anhydrous) and 37.8 kg of p-hydroxyphenylacetonitrile were charged into a stirred glass-lined reactor. 37.5 kg of hydrogen chloride gas were introduced through a dip tube at 10° C. within 5.5 hours. Crystals started to precipitate during the addition of hydrogen chloride, and a yellow to orange suspension resulted. For neutralization the reaction mixture was cooled to 5° C. 32 kg of methyl acetate, 330 kg of water and 103 kg of aqueous sodium hydroxide (28%, w/w) were added. Then methyl acetate was distilled off. Afterwards the reaction mixture was cooled down. At 70° C., 165 kg of ethanol were added and the reaction mixture was heated to reflux. Under these conditions, the iminium chloride was gradually dissolved and hydrolyzed. After 5 hours ethanol was distilled off to lower the solubility of phloroacetophenone. The reaction mixture was cooled down to 20° C. and the crystals were filtered off. The filter cake was washed with 2×30 kg of deionized water:ethanol (9:1, w/w). The crystals were dried at 90° C. for 8 hours.

The yield of phloroacetophenone was 78.6% based on phloroglucinol (purity 98.7%).

EXAMPLE 3

In a 250 ml reactor fitted with a magnetic stirrer, a dropping funnel, a distillation column, argon gasification means, a thermometer and a thermostat 6.9 g (87.5 mmol) of acetyl chloride were added dropwise to a stirred suspension of 6.1 g (88.4 mol) of sodium formate and 4.6 g (17.5 mmol) of phloroacetophenone in 26.3 g of acetone at a temperature of 12-15° C. under an argon atmosphere. The mixture was stirred at 23-25° C. for 2 hours. To the suspension were added 2.66 g (26.25 mmol) of triethylamine at 18-20° C. The reaction mixture was stirred at 21-22° C. for 2 hours and then heated at 30-32° C. for 1 hour. To promote the hydrolysis 11.6 g of 38% sulphuric acid were added dropwise to the suspension at room temperature. The solution was stirred at room temperature for about 16 hours. Then the mixture was heated to about 60° C. to remove about 30 g of distillate, and 14 g of ethanol were subsequently added to replace the lost solvent. The mixture was heated for a further 3 hours at about 70° C. The distillate which had accumulated consisted principally of acetone and a minor proportion of ethanol.

Following the distillation, 62 g of water were added to the remaining mixture in the reactor within 30 minutes, and the resulting slurry was then cooled to 30° C., stirred for a further hour and then filtered. The collected solid material was washed with 7 g of water at 35° C. and 8.8 g of ethanol/water (1:1) at 25° C. to afford 5.0 g of a moist, beige-coloured solid which was dried at 100° C./1 mbar (0.1 kPa) for 2 hours to yield 4.41 g of genistein as an off-white solid. The yield of genistein was calculated to be 91.7%, w/w (purity 98.4%).

EXAMPLE 4

In a 500 ml double-walled reactor fitted with a stirrer, a dropping funnel, a distillation column, argon gasification means, a thermometer and a thermostat 46.3 g (0.5 mol) of propionyl chloride were added dropwise to a stirred suspension of 35.7 g (0.505 mol) of sodium formate and 26.3 g (0.1 mol) of phloroacetophenone in 150 g of acetone at a temperature of 21-23° C. under an argon atmosphere. The mixture was stirred at 23-25° C. for 1 hour, then warmed to 30-32° C., stirred for 2 hours and finally cooled to 20° C. To the suspension were added 15.2 g (0.15 mol) of triethylamine at 20° C. The reaction mixture was stirred at 20-22° C. for 1 hour and then heated for 1.5 hours at 30-32° C. To promote the hydrolysis 66 g of 38% sulphuric acid were added dropwise to the suspension at room temperature. The solution was stirred at room temperature for about 16 hours. Then the mixture was heated to about 60° C. to remove about 156 g of distillate and 80 g of ethanol were subsequently added to replace the lost solvent. The mixture was heated for a further 3 hours at about 70° C. The distillate which had accumulated consisted principally of acetone and a minor proportion of ethanol.

Following the distillation, 350 g of water were added to the remaining mixture in the reactor within 30 minutes, and the resulting slurry was then cooled to 30° C., stirred for a further hour and then filtered. The collected solid material was washed twice with 40 g of water at 25° C. and 50 g of ethanol/water (1:1) at 5° C. to afford 34.4 g of a moist, beige-coloured solid which was dried at 100° C./1 mbar (0.1 kPa) for 2 hours to yield 26.0 g of genistein as an off-white solid. The yield of genistein was calculated to be 94.8%, w/w (purity 98.5%).

EXAMPLE 5

In a 500 ml double-walled reactor fitted with a stirrer, a dropping funnel, a distillation column, argon gasification means, a thermometer and a thermostat 54.4 g (0.5 mol) of isobutyryl chloride were added dropwise to a stirred suspension of 35.7 g (0.505 mol) of sodium formate and 26.3 g (0.1 mol) of phloroacetophenone in 150 g of acetone at a temperature of 21-23° C. under an argon atmosphere. The mixture was stirred at 23-25° C. for 1 hour, then warmed to 30-32° C., stirred for 2 hours and finally cooled to 18-20° C. To the suspension were added 15.2 g (0.15 mol) of triethylamine at 18-20° C. The reaction mixture was stirred at 21-22° C. for 1 hour and then heated at 30-32° C. for 1.5 hours. To promote the hydrolysis 50 g of 50% sulphuric acid were added dropwise to the suspension at room temperature. Then the mixture was heated to about 60° C. to remove about 148 g of distillate, and 120 g of ethanol were subsequently added to replace the lost solvent. The mixture was heated for a further 3 hours at about 70° C. The distillate which had accumulated consisted principally of acetone and a minor proportion of ethanol.

Following the distillation, 350 g of water were added to the remaining mixture in the reactor within 30 minutes, and the resulting slurry was then cooled to 30° C., stirred for a further hour and then filtered. The collected solid material was washed twice with 40 g of water at 35° C. and 50 g of ethanol/water (1:1) at 5° C. to afford 31.6 g of a moist, beige-coloured solid which was dried at 100° C./1 mbar (0.1 kPa) for 2 hours to yield 24.5 g of genistein as an off-white solid. The yield of genistein was calculated to be 90.2%, w/w (purity 99.7%).

EXAMPLE 6

To 103.5 g of anhydrous sodium formate (1.5 mol) in 658 ml of dimethylformamide at 0° C. were added 229.7 g of a sulfur trioxide-dimethylformamide complex (1.5 mol) in 658 ml of dimethylformamide within 1 hour and the reaction mixture was stirred for an additional hour to form a solution of sodium formylsulfate.

To 159.8 g of anhydrous sodium carbonate (1.5 mol) in 950 ml of dimethylformamide were added 99.6 g of anhydrous phloroacetophenone (375 mmol) and the resulting yellow suspension was stirred for 3 hours under argon at 25° C., then cooled to 0° C. To this suspension was added the above solution of sodium formylsulfate within 2 minutes and the reaction mixture was stirred for 18 hours at 0° C., heated to 80° C., and held at that temperature during 30 minutes. To the hot mixture were added within 40 minutes 732 ml of sulfuric acid (36%). After gas evolution had ceased, 2.44 l water-dimethylformamide was distilled off at 80° C. and 15 mbar. To the thick suspension were added within 1.5 hours at 70° C. 3.99 l of hot water (50° C.). The white suspension was stirred and cooled to 20° C. overnight, then filtered. The filter cake was washed 3 times with 272 ml of water, then dried at 60° C. at 12 mbar overnight to yield 101.9 g of genistein as a light beige solid. The calculated yield was 95% (purity 93%, w/w, HPLC).

The invention claimed is:

1. A process for manufacturing a hydroxylated isoflavone of the general formula

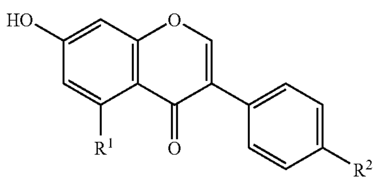

I wherein $R^1$, is hydrogen or hydroxy, and $R^2$ is hydroxy or $C_{1-6}$-alkoxy, by reacting in a Hoesch reaction using a $C_{1-5}$-alkanoic acid $C_{1-5}$-alkyl ester as solvent a phenol of the formula

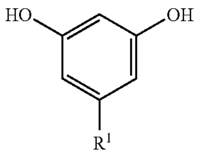

II with a phenylacetonitrile of the formula

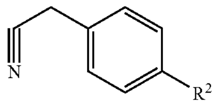

III to yield a 1,2-diphenyl-ethanone of formula

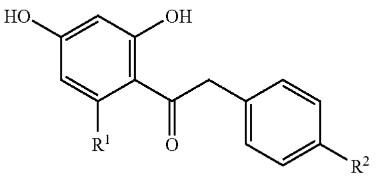

IV and further transforming the 1,2-diphenyl-ethanone into a compound of formula I.

2. A process for the preparation of a compound of formula I according to claim 1 wherein $R^1$ and $R^2$ are hydroxy.

3. A process as claimed in claim 1 wherein methyl acetate is used as solvent in the Hoesch reaction.

4. A process as claimed in claim 1 wherein ethyl acetate is used as solvent in the Hoesch reaction.

5. A process as claimed in claim 1 wherein the acid catalyst in the Hoesch reaction is gaseous hydrogen chloride.

6. A process as claimed in claim 1 wherein the intermediate ketiminium salt is hydrolysed in situ without being isolated.

7. A process as claimed in claim 1 wherein the transformation of the 1,2-diphenyl-ethanone of formula IV is effected with a mixed anhydride of formic acid.

8. A process as claimed in claim 7 wherein the mixed anhydride of formic acid is the mixed anhydride of formic and propionic acid.

9. A process as claimed in claim 7 wherein the mixed anhydride of formic acid is the mixed anhydride of formic and isobutyric acid.

10. A process for the preparation of a 1,2-diphenyl-ethanone of formula

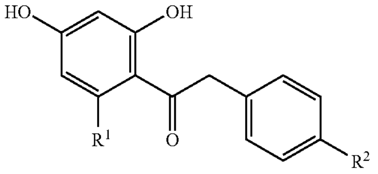

IV wherein $R^1$ is hydrogen or hydroxy and $R^2$ is hydroxy or $C_{1-6}$-alkoxy, which process comprises reacting in a Hoesch reaction using a $C_{1-5}$-alkanoic acid $C_{1-5}$-alkyl ester as solvent a phenol of the formula

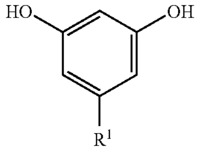

II with a phenylacetonitrile of the formula III

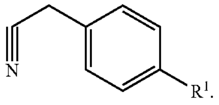

III

11. A process for the preparation of a 1,2-diphenyl-ethanone as claimed in claim 9 wherein $R^1$ and $R^2$ are hydroxy.

* * * * *